(12) United States Patent
Irwin et al.

(10) Patent No.: US 10,642,147 B2
(45) Date of Patent: May 5, 2020

(54) HYBRID PEROVSKITE MATERIAL PROCESSING

(71) Applicant: HEE Solar, L.L.C., Dallas, TX (US)

(72) Inventors: Michael D. Irwin, Dallas, TX (US); Kamil Mielczarek, Rowlett, TX (US); Vivek V. Dhas, Dallas, TX (US)

(73) Assignee: Hunt Perovskite Technologies LLC, Dallas, TX (US)

( * ) Notice: Subject to any disclaimer, the term of this patent is extended or adjusted under 35 U.S.C. 154(b) by 243 days.

(21) Appl. No.: 15/882,307

(22) Filed: Jan. 29, 2018

(65) Prior Publication Data

US 2018/0299764 A1 Oct. 18, 2018

Related U.S. Application Data

(62) Division of application No. 15/489,431, filed on Apr. 17, 2017, now Pat. No. 9,880,458.

(51) Int. Cl.
*G03C 8/36* (2006.01)
*B05D 3/10* (2006.01)
(Continued)

(52) U.S. Cl.
CPC ............... *G03C 8/365* (2013.01); *B05D 1/38* (2013.01); *B05D 3/107* (2013.01); *C01D 3/12* (2013.01);
(Continued)

(58) Field of Classification Search
CPC .......... B05D 1/38; B05D 3/107; G03C 8/365; G03C 2001/03558; C01D 3/12
See application file for complete search history.

(56) References Cited

U.S. PATENT DOCUMENTS 9,880,458 B1 1/2018 Irwin et al.
2015/0318477 A1\* 11/2015 Irwin .................. H01L 51/0003
556/35
(Continued)

FOREIGN PATENT DOCUMENTS

JP 2016-155766 A 9/2016
JP 2016155766 A \* 9/2016
KR 101561284 B1 10/2015

OTHER PUBLICATIONS

Choi, Hyosung; "Cesium-doped methylammonium lead iodide perovskite light absorber for hybrid solar cells," Nano Energy (2014) 7, pp. 80-85; published May 6, 2014.
(Continued)

*Primary Examiner* — Dah-Wei D. Yuan
*Assistant Examiner* — Kristen A Dagenais-Englehart
(74) *Attorney, Agent, or Firm* — Baker Botts L.L.P.

(57) ABSTRACT

A method for preparing photoactive perovskite materials. The method comprises the steps of: introducing a lead halide and a first solvent to a first vessel and contacting the lead halide with the first solvent to dissolve the lead halide to form a lead halide solution, introducing a Group 1 metal halide a second solvent into a second vessel and contacting the Group 1 metal halide with the second solvent to dissolve the Group 1 metal halide to form a Group 1 metal halide solution, and contacting the lead halide solution with the Group 1 metal halide solution to form a thin-film precursor ink. The method further comprises depositing the thin-film precursor ink onto a substrate, drying the thin-film precursor ink to form a thin film, annealing the thin film; and rinsing the thin film with a salt solution.

15 Claims, 7 Drawing Sheets

(51) Int. Cl.
- B05D 1/38 (2006.01)
- C01D 3/12 (2006.01)
- C07C 19/00 (2006.01)
- C01G 21/16 (2006.01)
- H01L 51/00 (2006.01)
- H01L 51/42 (2006.01)
- C09D 11/52 (2014.01)
- H01G 9/20 (2006.01)
- C07C 233/03 (2006.01)
- G03C 1/035 (2006.01)
- C07C 317/04 (2006.01)

(52) U.S. Cl.
CPC .............. *C01G 21/16* (2013.01); *C07C 19/00* (2013.01); *C09D 11/52* (2013.01); *H01G 9/2059* (2013.01); *H01L 51/0003* (2013.01); *H01L 51/4206* (2013.01); *H01L 51/4226* (2013.01); *C07C 233/03* (2013.01); *C07C 317/04* (2013.01); *G03C 2001/03558* (2013.01); *H01G 9/2009* (2013.01); *H01G 9/2031* (2013.01); *H01L 51/0007* (2013.01); *H01L 51/0026* (2013.01); *H01L 2251/306* (2013.01)

(56) References Cited

U.S. PATENT DOCUMENTS

2016/0035496 A1* 2/2016 Irwin .................. B05D 1/38
 136/265
2016/0268529 A1 9/2016 Irwin et al.

OTHER PUBLICATIONS

Xu, Feng et al., "Mixed cation hybrid lead halide perovskites with enhanced performance and stability", Journal of Materials Chemistry A, 2017, vol. 5, No. 23, pp. 11450-11461.

PCT, Notification of Transmittal of the International Search Report and the Written Opinion of the International Searching Authority, or the Declaration for PCT/US2018/027326, dated Jul. 30, 2018, 2 pages.

PCT, International Search Report for for PCT/US2018/027326, dated Jul. 30, 2018, 5 pages.

PCT, Written Opinion of the International Searching Authority for PCT/US2018/027326, dated Jul. 30, 2018, 4 pages.

\* cited by examiner

HYBRID PEROVSKITE MATERIAL PROCESSING

RELATED APPLICATION

This application is a division of U.S. application Ser. No. 15/489,431 filed Apr. 17, 2017 and entitled "Hybrid Perovskite Material Processing."

BACKGROUND

Use of photovoltaics (PVs) to generate electrical power from solar energy or radiation may provide many benefits, including, for example, a power source, low or zero emissions, power production independent of the power grid, durable physical structures (no moving parts), stable and reliable systems, modular construction, relatively quick installation, safe manufacture and use, and good public opinion and acceptance of use.

The features and advantages of the present disclosure will be readily apparent to those skilled in the art. While numerous changes may be made by those skilled in the art, such changes are within the spirit of the invention.

DETAILED DESCRIPTION OF PREFERRED EMBODIMENTS

Figure 1:
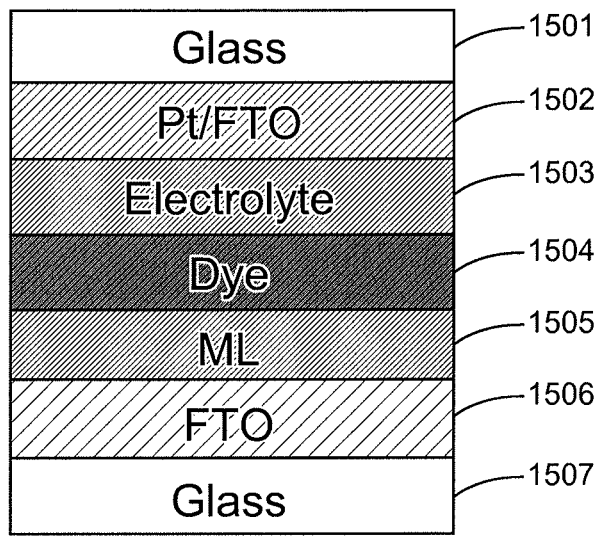
FIG. 1 is an illustration of DSSC design depicting various layers of the DSSC according to some embodiments of the present disclosure.

Improvements in various aspects of PV technologies compatible with organic, non-organic, and/or hybrid PVs promise to further lower the cost of both OPVs and other PVs. For example, some solar cells, such as solid-state dye-sensitized solar cells, may take advantage of novel cost-effective and high-stability alternative components, such as solid-state charge transport materials (or, colloquially, "solid state electrolytes"). In addition, various kinds of solar cells may advantageously include interfacial and other materials that may, among other advantages, be more cost-effective and durable than conventional options currently in existence.

The present disclosure relates generally to compositions of matter, apparatus and methods of use of materials in photovoltaic cells in creating electrical energy from solar radiation. More specifically, this disclosure relates to photoactive and other compositions of matter, as well as apparatus, methods of use, and formation of such compositions of matter.

Examples of these compositions of matter may include, for example, hole-transport materials, and/or materials that may be suitable for use as, e.g., interfacial layers, dyes, and/or other elements of PV devices. Such compounds may be deployed in a variety of PV devices, such as heterojunction cells (e.g., bilayer and bulk), hybrid cells (e.g., organics with $CH_3NH_3PbI_3$, ZnO nanorods or PbS quantum dots), and DSSCs (dye-sensitized solar cells). The latter, DSSCs, exist in three forms: solvent-based electrolytes, ionic liquid electrolytes, and solid-state hole transporters (or solid-state DSSCs, i.e., SS-DSSCs). SS-DSSC structures according to some embodiments may be substantially free of electrolyte, containing rather hole-transport materials such as spiro-OMeTAD, $CsSnI_3$, and other active materials.

Some or all of materials in accordance with some embodiments of the present disclosure may also advantageously be used in any organic or other electronic device, with some examples including, but not limited to: batteries, field-effect transistors (FETs), light-emitting diodes (LEDs), non-linear optical devices, memristors, capacitors, rectifiers, and/or rectifying antennas.

In some embodiments, the present disclosure may provide PV and other similar devices (e.g., batteries, hybrid PV batteries, multi junction PVs, FETs, LEDs etc.). Such devices may in some embodiments include improved active material, interfacial layers, and/or one or more perovskite materials. A perovskite material may be incorporated into various of one or more aspects of a PV or other device. A perovskite material according to some embodiments may be of the general formula CMX3, where: C comprises one or more cations (e.g., an amine, ammonium, a Group 1 metal, a Group 2 metal, and/or other cations or cation-like compounds); M comprises one or more metals (exemplars including Fe, Co, Ni, Cu, Sn, Pb, Bi, Ge, Ti, and Zr); and X comprises one or more anions. Perovskite materials according to various embodiments are discussed in greater detail below.

Photovoltaic Cells and Other Electronic Devices

Figure 3:
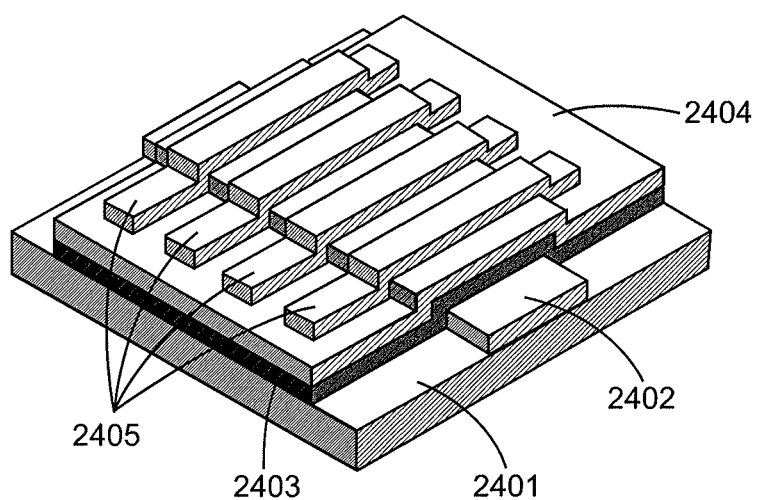
FIG. 3 is an example illustration of BHJ device design according to some embodiments of the present disclosure.
Figure 4:
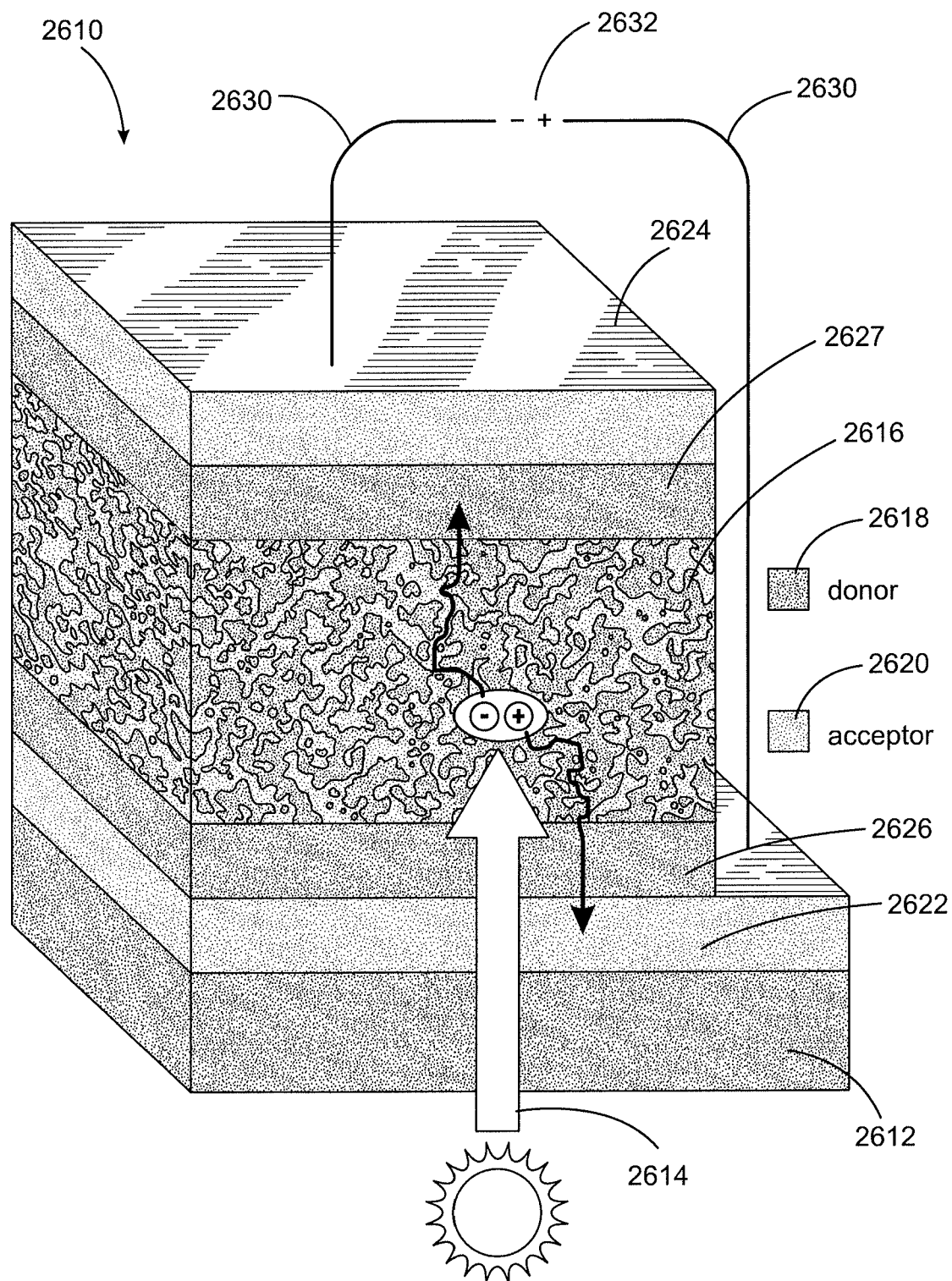
FIG. 4 is a schematic view of a typical photovoltaic cell including an active layer according to some embodiments of the present disclosure.

Some PV embodiments may be described by reference to various illustrative depictions of solar cells as shown in FIGS. 1, 3, 4, and 5. For example, an exemplary PV architecture according to some embodiments may be substantially of the form substrate-anode-IFL-active layer-IFL-cathode. The active layer of some embodiments may be photoactive, and/or it may include photoactive material. Other layers and materials may be utilized in the cell as is known in the art. Furthermore, it should be noted that the use of the term "active layer" is in no way meant to restrict or otherwise define, explicitly or implicitly, the properties of any other layer—for instance, in some embodiments, either or both IFLs may also be active insofar as they may be semiconducting. In particular, referring to FIG. 4, a stylized generic PV cell 2610 is depicted, illustrating the highly interfacial nature of some layers within the PV. The PV 2610 represents a generic architecture applicable to several PV devices, such as DSSC PV embodiments. The PV cell 2610 includes a transparent layer 2612 of glass (or material similarly transparent to solar radiation) which allows solar radiation 2614 to transmit through the layer. The transparent layer of some embodiments may also be referred to as a substrate (e.g., as with substrate layer 1507 of FIG. 1), and it may comprise any one or more of a variety of rigid or flexible materials such as: glass, polyethylene, PET, Kapton, quartz, aluminum foil, gold foil, or steel. The photoactive layer 2616 is composed of electron donor or p-type material 2618 and electron acceptor or n-type material 2620. The active layer or, as depicted in FIG. 4, the photo-active layer 2616, is sandwiched between two electrically conductive electrode layers 2622 and 2624. In FIG. 4, the electrode layer 2622 is an ITO material. As previously noted, an active layer of some embodiments need not necessarily be photoactive, although in the device shown in FIG. 4, it is. The electrode layer 2624 is an aluminum material. Other materials may be used as is known in the art. The cell 2610 also includes an interfacial layer (IFL) 2626, shown in the example of FIG. 4 as a PEDOT:PSS material. The IFL may assist in charge separation. In some embodiments, the IFL 2626 may comprise a photoactive organic compound according to the present disclosure as a self-assembled monolayer (SAM) or as a thin film. In other embodiments, the IFL 2626 may comprise a thin-coat bilayer, which is discussed in greater detail below. There also may be an IFL 2627 on the aluminum-cathode side of the device. In some embodiments, the IFL 2627 on the aluminum-cathode side of the device may also or instead comprise a photoactive organic compound according to the present disclosure as a self-assembled monolayer (SAM) or as a thin film. In other embodiments, the IFL 2627 on the aluminum-cathode side of the device may also or instead comprise a thin-coat bilayer (again, discussed in greater detail below). An IFL according to some embodiments may be semiconducting in character, and may be either p-type or n-type. In some embodiments, the IFL on the cathode side of the device (e.g., IFL 2627 as shown in FIG. 4) may be p-type, and the IFL on the anode side of the device (e.g., IFL 2626 as shown in FIG. 4) may be n-type. In other embodiments, however, the cathode-side IFL may be n-type and the anode-side IFL may be p-type. The cell 2610 is attached to leads 2630 and a discharge unit 2632, such as a battery.

Yet further embodiments may be described by reference to FIG. 3, which depicts a stylized BHJ device design, and includes: glass substrate 2401; ITO (tin-doped indium oxide) electrode 2402; interfacial layer (IFL) 2403; photoactive layer 2404; and LiF/Al cathodes 2405. The materials of BHJ construction referred to are mere examples; any other BHJ construction known in the art may be used consistent with the present disclosure. In some embodiments, the photoactive layer 2404 may comprise any one or more materials that the active or photoactive layer 2616 of the device of FIG. 4 may comprise.

Figure 2:
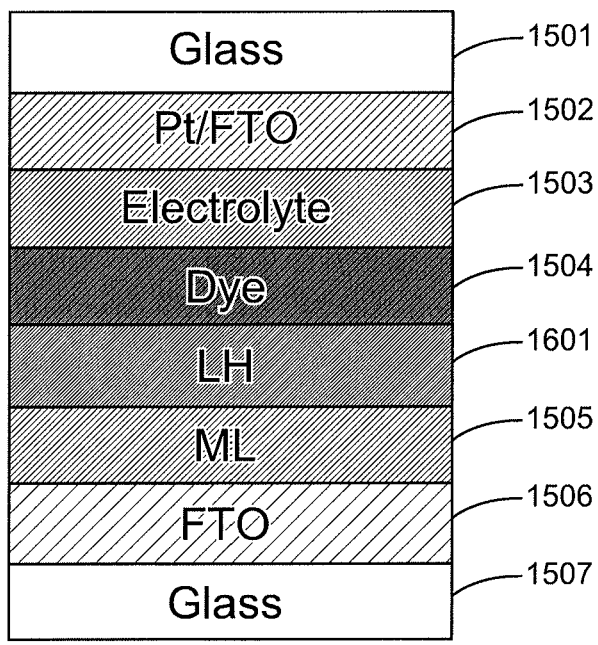
FIG. 2 is another illustration of DSSC design depicting various layers of the DSSC according to some embodiments of the present disclosure.

FIG. 1 is a simplified illustration of DSSC PVs according to some embodiments, referred to here for purposes of illustrating assembly of such example PVs. An example DSSC as shown in FIG. 1 may be constructed according to the following: electrode layer 1506 (shown as fluorine-doped tin oxide, FTO) is deposited on a substrate layer 1507 (shown as glass). Mesoporous layer ML 1505 (which may in some embodiments be $TiO_2$) is deposited onto the electrode layer 1506, then the photoelectrode (so far comprising substrate layer 1507, electrode layer 1506, and mesoporous layer 1505) is soaked in a solvent (not shown) and dye 1504. This leaves the dye 1504 bound to the surface of the ML. A separate counter-electrode is made comprising substrate layer 1501 (also shown as glass) and electrode layer 1502 (shown as Pt/FTO). The photoelectrode and counter-electrode are combined, sandwiching the various layers 1502-1506 between the two substrate layers 1501 and 1507 as shown in FIG. 1, and allowing electrode layers 1502 and 1506 to be utilized as a cathode and anode, respectively. A layer of electrolyte 1503 is deposited either directly onto the completed photoelectrode after dye layer 1504 or through an opening in the device, typically a hole pre-drilled by sandblasting in the counter-electrode substrate 1501. The cell may also be attached to leads and a discharge unit, such as a battery (not shown). Substrate layer 1507 and electrode layer 1506, and/or substrate layer 1501 and electrode layer 1502 should be of sufficient transparency to permit solar radiation to pass through to the photoactive dye 1504. In some embodiments, the counter-electrode and/or photoelectrode may be rigid, while in others either or both may be flexible. The substrate layers of various embodiments may comprise any one or more of: glass, polyethylene, PET, Kapton, quartz, aluminum foil, gold foil, and steel. In certain embodiments, a DSSC may further include a light harvesting layer 1601, as shown in FIG. 2, to scatter incident light in order to increase the light's path length through the photoactive layer of the device (thereby increasing the likelihood the light is absorbed in the photoactive layer).

In other embodiments, the present disclosure provides solid state DSSCs. Solid-state DSSCs according to some embodiments may provide advantages such as lack of leakage and/or corrosion issues that may affect DSSCs comprising liquid electrolytes. Furthermore, a solid-state charge carrier may provide faster device physics (e.g., faster charge transport). Additionally, solid-state electrolytes may, in some embodiments, be photoactive and therefore contribute to power derived from a solid-state DSSC device.

Figure 5:
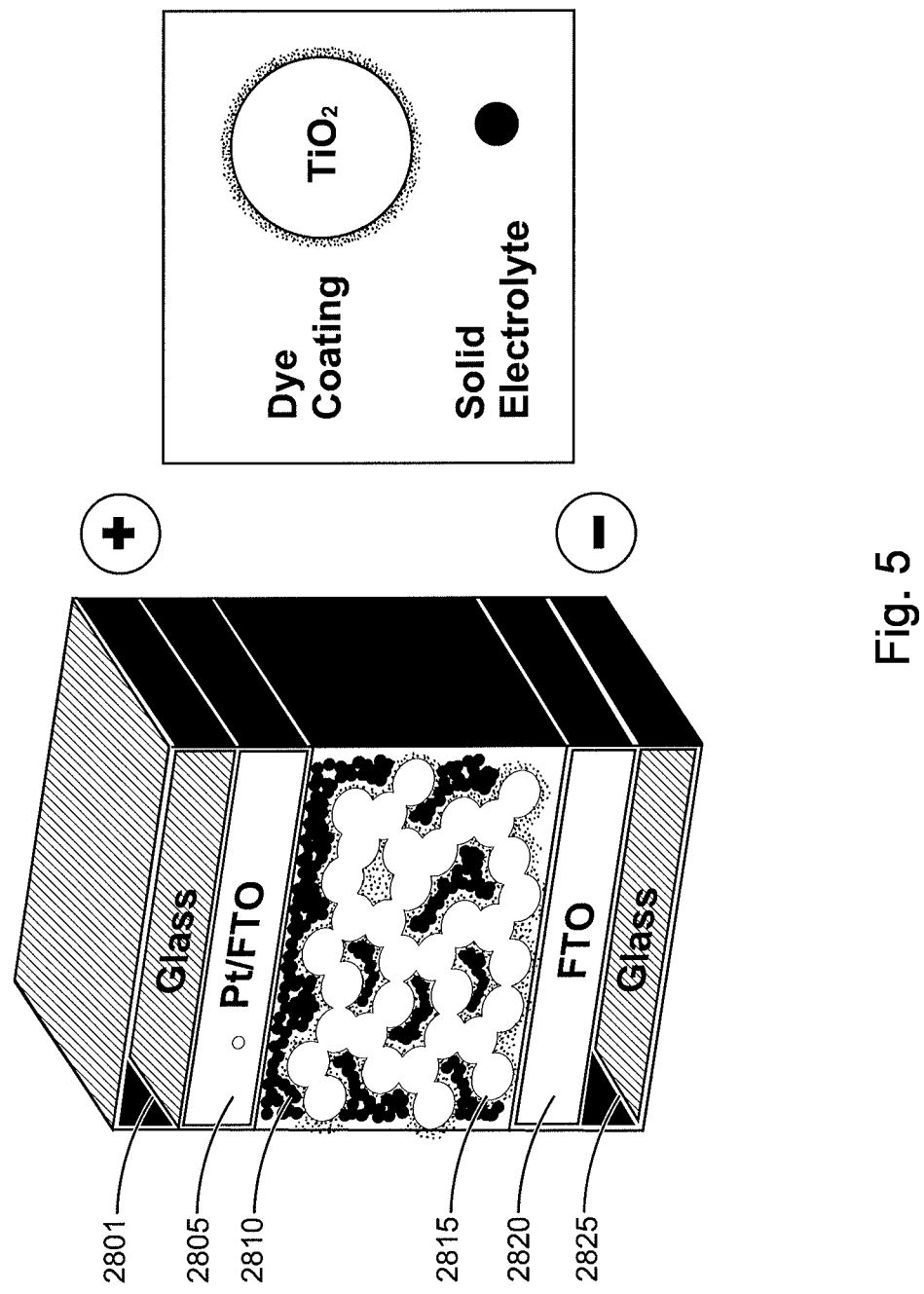
FIG. 5 is a schematic of a typical solid state DSSC device according to some embodiments of the present disclosure.

Some examples of solid state DSSCs may be described by reference to FIG. 5, which is a stylized schematic of a typical solid state DSSC. As with the example solar cell depicted in, e.g., FIG. 4, an active layer comprised of first and second active (e.g., conducting and/or semi-conducting) material (2810 and 2815, respectively) is sandwiched between electrodes 2805 and 2820 (shown in FIG. 5 as Pt/FTO and FTO, respectively). In the embodiment shown in FIG. 5, the first active material 2810 is p-type active material, and comprises a solid-state electrolyte. In certain embodiments, the first active material 2810 may comprise an organic material such as spiro-OMeTAD and/or poly(3-hexylthiophene), an inorganic binary, ternary, quaternary, or greater complex, any solid semiconducting material, or any combination thereof. In some embodiments, the first active material may additionally or instead comprise an oxide and/or a sulfide, and/or a selenide, and/or an iodide (e.g., $CsSnI_3$). Thus, for example, the first active material of some embodiments may comprise solid-state p-type material, which may comprise copper indium sulfide, and in some embodiments, it may comprise copper indium gallium selenide. The second active material 2815 shown in FIG. 5 is n-type active material and comprises $TiO_2$ coated with a dye. In some embodiments, the second active material may likewise comprise an organic material such as spiro-OMeTAD, an inorganic binary, ternary, quaternary, or greater complex, or any combination thereof. In some embodiments, the second active material may comprise an oxide such as alumina, and/or it may comprise a sulfide, and/or it may comprise a selenide. Thus, in some embodiments, the second active material may comprise copper indium sulfide, and in some embodiments, it may comprise copper indium gallium selenide metal. The second active material 2815 of some embodiments may constitute a mesoporous layer. Furthermore, in addition to being active, either or both of the first and second active materials 2810 and 2815 may be photoactive. In other embodiments (not shown in FIG. 5), the second active material may comprise a solid electrolyte. In addition, in embodiments where either of the first and second active material 2810 and 2815 comprise a solid electrolyte, the PV device may lack an effective amount of liquid electrolyte. Although shown and referred to in FIG. 5 as being p-type, a solid state layer (e.g., first active material comprising solid electrolyte) may in some embodiments instead be n-type semiconducting. In such embodiments, then, the second active material (e.g., $TiO_2$ (or other mesoporous material) as shown in FIG. 5) coated with a dye may be p-type semiconducting (as opposed to the n-type semiconducting shown in, and discussed with respect to, FIG. 5).

Substrate layers 2801 and 2825 (both shown in FIG. 5 as glass) form the respective external top and bottom layers of the exemplar cell of FIG. 5. These layers may comprise any material of sufficient transparency to permit solar radiation to pass through to the active/photoactive layer comprising dye, first and second active and/or photoactive material 2810 and 2815, such as glass, polyethylene, PET, Kapton, quartz, aluminum foil, gold foil, and/or steel. Furthermore, in the embodiment shown in FIG. 5, electrode 2805 (shown as Pt/FTO) is the cathode, and electrode 2820 is the anode. As with the exemplar solar cell depicted in FIG. 4, solar radiation passes through substrate layer 2825 and electrode 2820 into the active layer, whereupon at least a portion of the solar radiation is absorbed so as to produce one or more excitons to enable electrical generation.

A solid state DSSC according to some embodiments may be constructed in a substantially similar manner to that described above with respect to the DSSC depicted as stylized in FIG. 1. In the embodiment shown in FIG. 5, p-type active material 2810 corresponds to electrolyte 1503 of FIG. 1; n-type active material 2815 corresponds to both dye 1504 and ML 1505 of FIG. 1; electrodes 2805 and 2820 respectively correspond to electrode layers 1502 and 1506 of FIG. 1; and substrate layers 2801 and 2825 respectively correspond to substrate layers 1501 and 1507.

Various embodiments of the present disclosure provide improved materials and/or designs in various aspects of solar cell and other devices, including among other things, active materials (including hole-transport and/or electron-transport layers), interfacial layers, and overall device design.

Interfacial Layers

The present disclosure in some embodiments provides advantageous materials and designs of one or more interfacial layers within a PV, including thin-coat IFLs. Thin-coat IFLs may be employed in one or more IFLs of a PV according to various embodiments discussed herein.

First, as previously noted, one or more IFLs (e.g., either or both IFLs 2626 and 2627 as shown in FIG. 4) may comprise a photoactive organic compound of the present disclosure as a self-assembled monolayer (SAM) or as a thin film. When a photoactive organic compound of the present disclosure is applied as a SAM, it may comprise a binding group through which it may be covalently or otherwise bound to the surface of either or both of the anode and cathode. The binding group of some embodiments may comprise any one or more of COOH, $SiX_3$ (where X may be any moiety suitable for forming a ternary silicon compound, such as $Si(OR)_3$ and $SiCl_3$), $SO_3$, $PO_4H$, OH, $CH_2X$ (where X may comprise a Group 17 halide), and O. The binding group may be covalently or otherwise bound to an electron-withdrawing moiety, an electron donor moiety, and/or a core moiety. The binding group may attach to the electrode surface in a manner so as to form a directional, organized layer of a single molecule (or, in some embodiments, multiple molecules) in thickness (e.g., where multiple photoactive organic compounds are bound to the anode and/or cathode). As noted, the SAM may attach via covalent interactions, but in some embodiments it may attach via ionic, hydrogen-bonding, and/or dispersion force (i.e., Van Der Waals) interactions. Furthermore, in certain embodiments, upon light exposure, the SAM may enter into a zwitterionic excited state, thereby creating a highly-polarized IFL, which may direct charge carriers from an active layer into an electrode (e.g., either the anode or cathode). This enhanced charge-carrier injection may, in some embodiments, be accomplished by electronically poling the cross-section of the active layer and therefore increasing charge-carrier drift velocities towards their respective electrode (e.g., hole to anode; electrons to cathode). Molecules for anode applications of some embodiments may comprise tunable compounds that include a primary electron donor moiety bound to a core moiety, which in turn is bound to an electron-withdrawing moiety, which in turn is bound to a binding group. In cathode applications according to some embodiments, IFL molecules may comprise a tunable compound comprising an electron poor moiety bound to a core moiety, which in turn is bound to an electron donor moiety, which in turn is bound to a binding group. When a photoactive organic compound is employed as an IFL according to such embodiments, it may retain photoactive character, although in some embodiments it need not be photoactive.

In addition or instead of a photoactive organic compound SAM IFL, a PV according to some embodiments may include a thin interfacial layer (a "thin-coat interfacial layer" or "thin-coat IFL") coated onto at least a portion of either the first or the second active material of such embodiments (e.g., first or second active material 2810 or 2815 as shown in FIG. 5). And, in turn, at least a portion of the thin-coat IFL may be coated with a dye. The thin-coat IFL may be either n- or p-type; in some embodiments, it may be of the same type as the underlying material (e.g., $TiO_2$ or other mesoporous material, such as $TiO_2$ of second active material 2815). The second active material may comprise $TiO_2$ coated with a thin-coat IFL comprising alumina (e.g., $Al_2O_3$) (not shown in FIG. 5), which in turn is coated with a dye. References herein to $TiO_2$ and/or titania are not intended to limit the ratios of tin and oxide in such tin-oxide compounds described herein. That is, a titania compound may comprise titanium in any one or more of its various oxidation states (e.g., titanium I, titanium II, titanium III, titanium IV), and thus various embodiments may include stoichiometric and/or non-stoichiometric amounts of titanium and oxide. Thus, various embodiments may include (instead or in addition to $TiO_2$) $Ti_xO_y$, where x may be any value, integer or non-integer, between 1 and 100. In some embodiments, x may be between approximately 0.5 and 3. Likewise, y may be between approximately 1.5 and 4 (and, again, need not be an integer). Thus, some embodiments may include, e.g., $TiO_2$ and/or $Ti_2O_3$. In addition, titania in whatever ratios or combination of ratios between titanium and oxide may be of any one or more crystal structures in some embodiments, including any one or more of anatase, rutile, and amorphous.

Other exemplary metal oxides for use in the thin-coat IFL of some embodiments may include semiconducting metal oxides, such as ZnO, $ZrO_2$, $Nb_2O_5$, $SrTiO_3$, $Ta_2O_3$, NiO, $WO_3$, $V_2O_5$, or $MoO_3$. The exemplar embodiment wherein the second (e.g., n-type) active material comprises $TiO_2$ coated with a thin-coat IFL comprising $Al_2O_3$ could be formed, for example, with a precursor material such as $Al(NO_3)_3 \cdot xH_2O$, or any other material suitable for depositing $Al_2O_3$ onto the $TiO_2$, followed by thermal annealing and dye coating. In example embodiments wherein a $MoO_3$ coating is instead used, the coating may be formed with a precursor material such as $Na_2Mo_4.2H_2O$; whereas a $V_2O_5$ coating according to some embodiments may be formed with a precursor material such as $NaVO_3$; and a $WO_3$ coating according to some embodiments may be formed with a precursor material such as $NaWO_4.H_2O$. The concentration of precursor material (e.g., $Al(NO_3)_3.xH_2O$) may affect the final film thickness (here, of $Al_2O_3$) deposited on the $TiO_2$ or other active material. Thus, modifying the concentration of precursor material may be a method by which the final film thickness may be controlled. For example, greater film thickness may result from greater precursor material concentration. Greater film thickness may not necessarily result in greater PCE in a PV device comprising a metal oxide coating. Thus, a method of some embodiments may include coating a $TiO_2$ (or other mesoporous) layer using a precursor material having a concentration in the range of approximately 0.5 to 10.0 mM; other embodiments may include coating the layer with a precursor material having a concentration in the range of approximately 2.0 to 6.0 mM; or, in other embodiments, approximately 2.5 to 5.5 mM.

Furthermore, although referred to herein as $Al_2O_3$ and/or alumina, it should be noted that various ratios of aluminum and oxygen may be used in forming alumina. Thus, although some embodiments discussed herein are described with reference to $Al_2O_3$, such description is not intended to define a required ratio of aluminum in oxygen. Rather, embodiments may include any one or more aluminum-oxide compounds, each having an aluminum oxide ratio according to $Al_xO_y$, where x may be any value, integer or non-integer, between approximately 1 and 100. In some embodiments, x may be between approximately 1 and 3 (and, again, need not be an integer). Likewise, y may be any value, integer or non-integer, between 0.1 and 100. In some embodiments, y may be between 2 and 4 (and, again, need not be an integer). In addition, various crystalline forms of $Al_xO_y$ may be present in various embodiments, such as alpha, gamma, and/or amorphous forms of alumina.

Likewise, although referred to herein as $MoO_3$, $WO_3$, and $V_2O_5$, such compounds may instead or in addition be represented as $Mo_xO_y$, $W_xO_y$, and $V_xO_y$, respectively. Regarding each of $Mo_xO_y$ and $W_xO_y$, x may be any value, integer or non-integer, between approximately 0.5 and 100; in some embodiments, it may be between approximately 0.5 and 1.5. Likewise, y may be any value, integer or non-integer, between approximately 1 and 100. In some embodiments, y may be any value between approximately 1 and 4. Regarding $V_xO_y$, x may be any value, integer or non-integer, between approximately 0.5 and 100; in some embodiments, it may be between approximately 0.5 and 1.5. Likewise, y may be any value, integer or non-integer, between approximately 1 and 100; in certain embodiments, it may be an integer or non-integer value between approximately 1 and 10.

Similarly, references in some exemplar embodiments herein to $CsSnI_3$ are not intended to limit the ratios of component elements in the cesium-tin-iodine compounds according to various embodiments. Some embodiments may include stoichiometric and/or non-stoichiometric amounts of tin and iodide, and thus such embodiments may instead or in addition include various ratios of cesium, tin, and iodine, such as any one or more cesium-tin-iodine compounds, each having a ratio of $Cs_xSn_yI_z$. In such embodiments, x may be any value, integer or non-integer, between 0.1 and 100. In some embodiments, x may be between approximately 0.5 and 1.5 (and, again, need not be an integer). Likewise, y may be any value, integer or non-integer, between 0.1 and 100. In some embodiments, y may be between approximately 0.5 and 1.5 (and, again, need not be an integer). Likewise, z may be any value, integer or non-integer, between 0.1 and 100. In some embodiments, z may be between approximately 2.5 and 3.5. Additionally $CsSnI_3$ can be doped or compounded with other materials, such as $SnF_2$, in ratios of $CsSnI_3:SnF_2$ ranging from 0.1:1 to 100:1, including all values (integer and non-integer) in between.

In addition, a thin-coat IFL may comprise a bilayer. Thus, returning to the example wherein the thin-coat IFL comprises a metal-oxide (such as alumina), the thin-coat IFL may comprise $TiO_2$-plus-metal-oxide. Such a thin-coat IFL may have a greater ability to resist charge recombination as compared to mesoporous $TiO_2$ or other active material alone. Furthermore, in forming a $TiO_2$ layer, a secondary $TiO_2$ coating is often necessary in order to provide sufficient physical interconnection of $TiO_2$ particles, according to some embodiments of the present disclosure. Coating a bilayer thin-coat IFL onto mesoporous $TiO_2$ (or other mesoporous active material) may comprise a combination of coating using a compound comprising both metal oxide and $TiCl_4$, resulting in an bilayer thin-coat IFL comprising a combination of metal-oxide and secondary $TiO_2$ coating, which may provide performance improvements over use of either material on its own.

The thin-coat IFLs and methods of coating them onto $TiO_2$ previously discussed may, in some embodiments, be employed in DSSCs comprising liquid electrolytes. Thus, returning to the example of a thin-coat IFL and referring back to FIG. 1 for an example, the DSSC of FIG. 1 could further comprise a thin-coat IFL as described above coated onto the mesoporous layer 1505 (that is, the thin-coat IFL would be inserted between mesoporous layer 1505 and dye 1504).

In some embodiments, the thin-coat IFLs previously discussed in the context of DSSCs may be used in any interfacial layer of a semiconductor device such as a PV (e.g., a hybrid PV or other PV), field-effect transistor, light-emitting diode, non-linear optical device, memristor, capacitor, rectifier, rectifying antenna, etc. Furthermore, thin-coat IFLs of some embodiments may be employed in any of various devices in combination with other compounds discussed in the present disclosure, including but not limited to any one or more of the following of various embodiments of the present disclosure: solid hole-transport material such as active material and additives (such as, in some embodiments, chenodeoxycholic acid or 1,8-diiodooctane).

Additives

As previously noted, PV and other devices according to some embodiments may include additives (which may be, e.g., any one or more of acetic acid, propanoic acid, trifluoroacetic acid, chenodeoxycholic acid, deoxycholic acid, 1,8-diiodooctane, and 1,8-dithiooctane). Such additives may be employed as pretreatments directly before dye soaking or mixed in various ratios with a dye to form the soaking solution. These additives may in some instances function, for example, to increase dye solubility, preventing dye molecule clustering, by blocking open active sites, and by inducing molecular ordering amongst dye molecules. They may be employed with any suitable dye, including a photoactive compound according to various embodiments of the present disclosure as discussed herein.

Perovskite Material

A perovskite material may be incorporated into one or more aspects of a PV or other device. A perovskite material according to some embodiments may be of the general formula $C_wM_yX_z$, where: C comprises one or more cations (e.g., an amine, ammonium, a Group 1 metal, a Group 2 metal, and/or other cations or cation-like compounds); M comprises one or more metals (examples including Fe, Co, Ni, Cu, Ag, Au, Tl, In, Sb, Sn, Pb, Bi, Ga, Ge, Ti, and Zn); X comprises one or more anions; and w, y, and z represent real numbers between 1 and 20. In some embodiments, C may include one or more organic cations. In some embodiments, each organic cation C may be larger than each metal M, and each anion X may be capable of bonding with both a cation C and a metal M. In particular embodiments, a perovskite material may be of the formula $CMX_3$.

In certain embodiments, C may include an ammonium, an organic cation of the general formula $[NR_4]^+$ where the R groups may be the same or different groups. Suitable R groups include, but are not limited to: methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., pyridine, pyrrole, pyrrolidine, piperidine, tetrahydroquinoline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (e.g., acetic acid, propanoic acid); and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OCxHy, where x=0-20, y=1-42.

In certain embodiments, C may include a formamidinium, an organic cation of the general formula $[R_2NCRNR_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., imidazole, benzimidazole, dihydropyrimidine, (azolidinylidenemethyl)pyrrolidine, triazole); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OCxHy, where x=0-20, y=1-42.

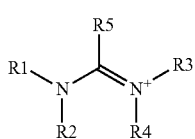

Formula 1

Formula 1 illustrates the structure of a formamidinium cation having the general formula of $[R_2NCRNR_2]^+$ as described above. Formula 2 illustrates examples structures of several formamidinium cations that may serve as a cation "C" in a perovskite material.

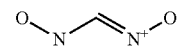

Formula 2

Hydroxy-[(hydroxyamino)methylene]ammonium

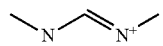

Methyl(methylaminomethylene)ammonium

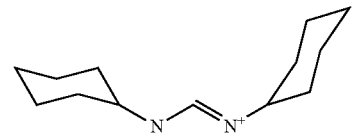

Cyclohexyl-[(cyclohexylamino)methylene]ammonium

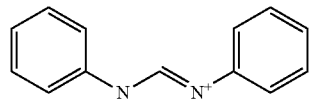

Anilinomethylene(phenyl)ammonium

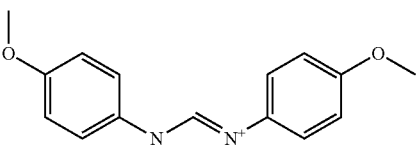

(Methoxyanilino)methylene-(4-methoxyphenyl)ammonium

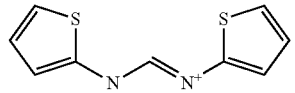

Thienyl-[(2-thienylamino)methylene]ammonium

In certain embodiments, C may include a guanidinium, an organic cation of the general formula $[(R_2N)_2C=NR_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., octahydropyrimido[1,2-a]pyrimidine, pyrimido[1,2-a]pyrimidine, hexahydroimidazo[1,2-a]imidazole, hexahydropyrimidin-2-imine); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OCxHy, where x=0-20, y=1-42.

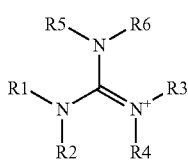

Formula 3

Formula 3 illustrates the structure of a guanidinium cation having the general formula of $[(R_2N)_2C=NR_2]^+$ as described above. Formula 4 illustrates examples of structures of several guanidinium cations that may serve as a cation "C" in a perovskite material.

Formula 4

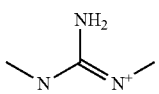

[Amino(methylamino)methylene]-methyl-ammonium

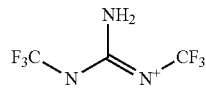

[Amino-(trifluoromethylamino)methylene]-(trifluoromethyl)ammonium

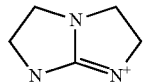

2,3,5,6-Tetrahydro-1H-imidazo[1,2-a]imidazol-7-ium

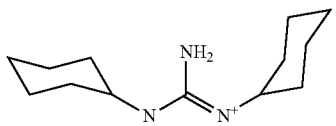

[Amino-(cyclohexylamino)methylene]-cyclohexyl-ammonium

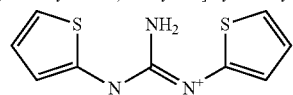

[Amino-(2-thienylamino)methylene]-(2-thienyl)ammonium

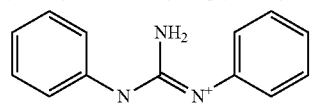

[Amino-(anilino)methylene]-phenyl-ammonium

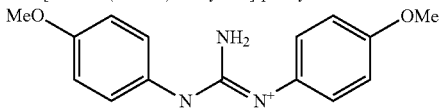

[Amino-(4-methoxyanilino)methylene]-(4-methoxyphenyl)ammonium

In certain embodiments, C may include an ethene tetramine cation, an organic cation of the general formula $[(R_2N)_2C=C(NR_2)_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., 2-hexahydropyrimidin-2-ylidenehexahydropyrimidine, octahydropyrazino[2,3-b]pyrazine, pyrazino[2,3-b]pyrazine, quinoxalino[2,3-b]quinoxaline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OCxHy, where x=0-20, y=1-42.

Formula 5

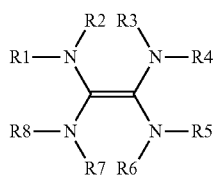

Formula 5 illustrates the structure of an ethene tetramine cation having the general formula of $[(R_2N)_2C=C(NR_2)_2]^+$ as described above. Formula 6 illustrates examples of structures of several ethene tetramine ions that may serve as a cation "C" in a perovskite material.

Formula 6

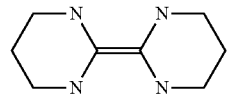

2-hexahydropyrimidin-2-ylidenehexahydropyrimidine

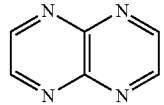

pyrazino[2,3-b]pyrazine

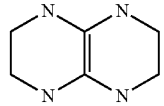

1,2,3,4,5,6,7,8-octahydropyrazino[2,3-b]pyrazine

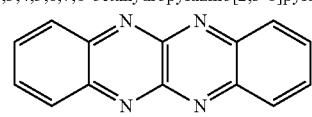

quinoxalino[2,3-b]quinoxaline

In certain embodiments, C may include an imidazolium cation, an aromatic, cyclic organic cation of the general formula [CRNRCRNRCR]+ where the R groups may be the same or different groups. Suitable R groups may include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., 2-hexahydropyrimidin-2-ylidenehexahydropyrimidine, octahydropyrazino[2,3-b]pyrazine, pyrazino[2,3-b]pyrazine, quinoxalino[2,3-b]quinoxaline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OCxHy, where x=0-20, y=1-42.

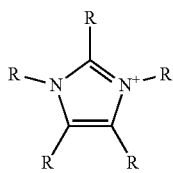

Formula 7

In some embodiments, X may include one or more halides. In certain embodiments, X may instead or in addition include a Group 16 anion. In certain embodiments, the Group 16 anion may be sulfide or selenide. In certain embodiments, X may instead or in addition include one or more a pseudohalides (e.g., cyanide, cyanate, isocyanate, fulminate, thiocyanate, isothiocyanate, azide, tetracarbonylcobaltate, carbamoyldicyanomethanide, dicyanonitrosomethanide, dicyanamide, and tricyanomethanide).

In one embodiment, a perovskite material may comprise the empirical formula $CMX_3$ where: C comprises one or more of the aforementioned cations, a Group 1 metal, a Group 2 metal, and/or other cations or cation-like compounds; M comprises one or more metals (examples including Fe, Co, Ni, Cu, Ag, Au, Sb, Sn, Pb, Bi, Ga, Ge, Ti, Tl, and Zn); and X comprises one or more of the aforementioned anions.

In one embodiment, a perovskite material may comprise the empirical formula $C_3M_2X_9$ where: C comprises one or more of the aforementioned cations, a Group 1 metal, a Group 2 metal, and/or other cations or cation-like compounds; M comprises one or more metals (examples including Fe, Co, Ni, Cu, Ag, Au, Sb, Sn, Pb, Bi, Ga, Ge, Ti, Tl, and Zn); and X comprises one or more of the aforementioned anions.

In one embodiment, a perovskite material may comprise the empirical formula $CM_2X_7$ where: C comprises one or more of the aforementioned cations, a Group 1 metal, a Group 2 metal, and/or other cations or cation-like compounds; M comprises one or more metals (examples including Fe, Co, Ni, Cu, Ag, Au, Sb, Sn, Pb, Bi, Ga, Ge, Ti, Tl, and Zn); and X comprises one or more of the aforementioned anions.

In one embodiment, a perovskite material may comprise the empirical formula $C_2MX_4$ where: C comprises one or more of the aforementioned cations, a Group 1 metal, a Group 2 metal, and/or other cations or cation-like compounds; M comprises one or more metals (examples including Fe, Co, Ni, Cu, Ag, Au, Sb, Sn, Pb, Bi, Ga, Ge, Ti, Tl, and Zn); and X comprises one or more of the aforementioned anions.

Perovskite materials may also comprise mixed ion formulations where C, M, or X comprise two or more species, for example, $Cs_{0.1}FA_{0.9}PbI_3$; $FAPb_{0.5}Sn_{0.5}I_3$; $FA_{0.83}Cs_{0.17}Pb(I_{0.6}Br_{0.4})_3$; $FA_{0.83}Cs_{0.12}Rb_{0.05}Pb(I_{0.6}Br_{0.4})_3$ and $FA_{0.85}MA_{0.15}Pb(I_{0.85}Br_{0.15})_3$. Examples of perovskite materials according to various embodiments include $CsSnI_3$ (previously discussed herein) and $Cs_xSn_yI_z$ (with x, y, and z varying in accordance with the previous discussion). Other examples include compounds of the general formula $CsSnX_3$, where X may be any one or more of: $I_3$, $I_{2.95}F_{0.05}$; $I_2Cl$; $ICl_2$; and $Cl_3$. In other embodiments, X may comprise any one or more of I, Cl, F, and Br in amounts such that the total ratio of X as compared to Cs and Sn results in the general stoichiometry of $CsSnX_3$. In some embodiments, the combined stoichiometry of the elements that constitute X may follow the same rules as $I_z$ as previously discussed with respect to $Cs_xSn_yI_z$. Yet other examples include compounds of the general formula $RNH_3PbX_3$, where R may be $C_nH_{2n+1}$, with n ranging from 0-10, and X may include any one or more of F, Cl, Br, and I in amounts such that the total ratio of X as compared to the cation $RNH_3$ and metal Pb results in the general stoichiometry of $RNH_3PbX_3$. Further, some specific examples of R include H, alkyl chains (e.g., $CH_3$, $CH_3CH_2$, $CH_3CH_2CH_2$, and so on), and amino acids (e.g., glycine, cysteine, proline, glutamic acid, arginine, serine, histindine, 5-ammoniumvaleric acid) including alpha, beta, gamma, and greater derivatives.

Composite Perovskite Material Device Design

In some embodiments, the present disclosure may provide composite design of PV and other similar devices (e.g., batteries, hybrid PV batteries, FETs, LEDs etc.) including one or more perovskite materials. For example, one or more perovskite materials may serve as either or both of first and second active material of some embodiments (e.g., active materials 2810 and 2815 of FIG. 5). In more general terms, some embodiments of the present disclosure provide PV or other devices having an active layer comprising one or more perovskite materials. In such embodiments, perovskite material (that is, material including any one or more perovskite materials(s)) may be employed in active layers of various architectures. Furthermore, perovskite material may serve the function(s) of any one or more components of an active layer (e.g., charge transport material, mesoporous material, photoactive material, and/or interfacial material, each of which is discussed in greater detail below). In some embodiments, the same perovskite materials may serve multiple such functions, although in other embodiments, a plurality of perovskite materials may be included in a device, each perovskite material serving one or more such functions. In certain embodiments, whatever role a perovskite material may serve, it may be prepared and/or present in a device in various states. For example, it may be substantially solid in some embodiments. In other embodiments, it may be a solution (e.g., perovskite material may be dissolved in liquid and present in said liquid in its individual ionic subspecies); or it may be a suspension (e.g., of perovskite material particles). A solution or suspension may be coated or otherwise deposited within a device (e.g., on another component of the device such as a mesoporous, interfacial, charge transport, photoactive, or other layer, and/or on an electrode). Perovskite materials in some embodiments may be formed in situ on a surface of another component of a device (e.g., by vapor deposition as a thin-film solid). Any other suitable means of forming a solid or liquid layer comprising perovskite material may be employed.

In general, a perovskite material device may include a first electrode, a second electrode, and an active layer comprising a perovskite material, the active layer disposed at least partially between the first and second electrodes. In some embodiments, the first electrode may be one of an anode and a cathode, and the second electrode may be the other of an anode and cathode. An active layer according to certain embodiments may include any one or more active layer components, including any one or more of: charge transport material; liquid electrolyte; mesoporous material; photoactive material (e.g., a dye, silicon, cadmium telluride, cadmium sulfide, cadmium selenide, copper indium gallium selenide, gallium arsenide, germanium indium phosphide, semiconducting polymers, other photoactive materials)); and interfacial material. Any one or more of these active layer components may include one or more perovskite materials. In some embodiments, some or all of the active layer components may be in whole or in part arranged in sub-layers. For example, the active layer may comprise any one or more of: an interfacial layer including interfacial material; a mesoporous layer including mesoporous material; and a charge transport layer including charge transport material. In some embodiments, photoactive material such as a dye may be coated on, or otherwise disposed on, any one or more of these layers. In certain embodiments, any one or more layers may be coated with a liquid electrolyte. Further, an interfacial layer may be included between any two or more other layers of an active layer according to some embodiments, and/or between a layer and a coating (such as between a dye and a mesoporous layer), and/or between two coatings (such as between a liquid electrolyte and a dye), and/or between an active layer component and an electrode. Reference to layers herein may include either a final arrangement (e.g., substantially discrete portions of each material separately definable within the device), and/or reference to a layer may mean arrangement during construction of a device, notwithstanding the possibility of subsequent intermixing of material(s) in each layer. Layers may in some embodiments be discrete and comprise substantially contiguous material (e.g., layers may be as stylistically illustrated in FIG. 1). In other embodiments, layers may be substantially intermixed (as in the case of, e.g., BHJ, hybrid, and some DSSC cells), an example of which is shown by first and second active material 2618 and 2620 within photoactive layer 2616 in FIG. 4. In some embodiments, a device may comprise a mixture of these two kinds of layers, as is also shown by the device of FIG. 4, which contains discrete contiguous layers 2627, 2626, and 2622, in addition to a photoactive layer 2616 comprising intermixed layers of first and second active material 2618 and 2620. In any case, any two or more layers of whatever kind may in certain embodiments be disposed adjacent to each other (and/or intermixedly with each other) in such a way as to achieve a high contact surface area. In certain embodiments, a layer comprising perovskite material may be disposed adjacent to one or more other layers so as to achieve high contact surface area (e.g., where a perovskite material exhibits low charge mobility). In other embodiments, high contact surface area may not be necessary (e.g., where a perovskite material exhibits high charge mobility).

A perovskite material device according to some embodiments may optionally include one or more substrates. In some embodiments, either or both of the first and second electrode may be coated or otherwise disposed upon a substrate, such that the electrode is disposed substantially between a substrate and the active layer. The materials of composition of devices (e.g., substrate, electrode, active layer and/or active layer components) may in whole or in part be either rigid or flexible in various embodiments. In some embodiments, an electrode may act as a substrate, thereby negating the need for a separate substrate.

Furthermore, a perovskite material device according to certain embodiments may optionally include light-harvesting material (e.g., in a light-harvesting layer, such as Light Harvesting Layer 1601 as depicted in the exemplary PV represented in FIG. 2). In addition, a perovskite material device may include any one or more additives, such as any one or more of the additives discussed above with respect to some embodiments of the present disclosure.

Figure 7:
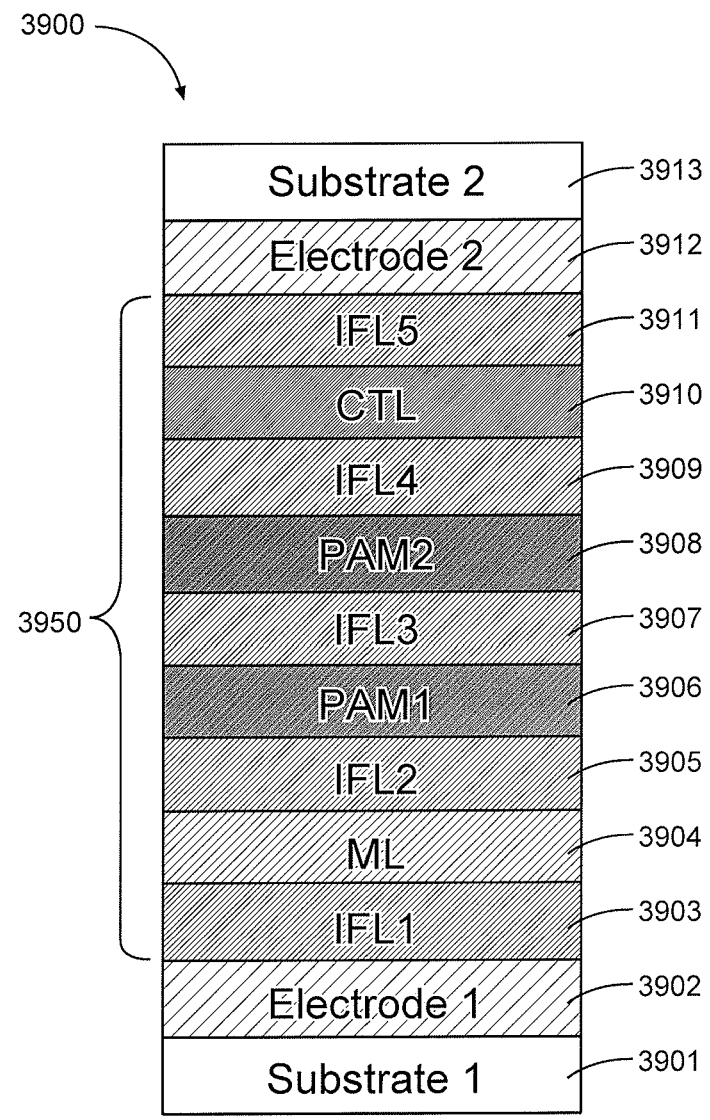
FIG. 7 is a stylized diagram showing components of an exemplar PV device according to some embodiments of the present disclosure.

Description of some of the various materials that may be included in a perovskite material device will be made in part with reference to FIG. 7. FIG. 7 is a stylized diagram of a perovskite material device 3900 according to some embodiments. Although various components of the device 3900 are illustrated as discrete layers comprising contiguous material, it should be understood that FIG. 7 is a stylized diagram; thus, embodiments in accordance with it may include such discrete layers, and/or substantially intermixed, non-contiguous layers, consistent with the usage of "layers" previously discussed herein. The device 3900 includes first and second substrates 3901 and 3913. A first electrode 3902 is disposed upon an inner surface of the first substrate 3901, and a second electrode 3912 is disposed on an inner surface of the second substrate 3913. An active layer 3950 is sandwiched between the two electrodes 3902 and 3912. The active layer 3950 includes a mesoporous layer 3904; first and second photoactive materials 3906 and 3908; a charge transport layer 3910, and several interfacial layers. FIG. 7 furthermore illustrates an example device 3900 according to embodiments wherein sub-layers of the active layer 3950 are separated by the interfacial layers, and further wherein interfacial layers are disposed upon each electrode 3902 and 3912. In particular, second, third, and fourth interfacial layers 3905, 3907, and 3909 are respectively disposed between each of the mesoporous layer 3904, first photoactive material 3906, second photoactive material 3908, and charge transport layer 3910. First and fifth interfacial layers 3903 and 3911 are respectively disposed between (i) the first electrode 3902 and mesoporous layer 3904; and (ii) the charge transport layer 3910 and second electrode 3912. Thus, the architecture of the example device depicted in FIG. 7 may be characterized as: substrate-electrode-active layer-electrode-substrate. The architecture of the active layer 3950 may be characterized as: interfacial layer-mesoporous layer-interfacial layer-photoactive material-interfacial layer-photoactive material-interfacial layer-charge transport layer-interfacial layer. As noted previously, in some embodiments, interfacial layers need not be present; or, one or more interfacial layers may be included only between certain, but not all, components of an active layer and/or components of a device.

A substrate, such as either or both of first and second substrates 3901 and 3913, may be flexible or rigid. If two substrates are included, at least one should be transparent or translucent to electromagnetic (EM) radiation (such as, e.g., UV, visible, or IR radiation). If one substrate is included, it may be similarly transparent or translucent, although it need not be, so long as a portion of the device permits EM radiation to contact the active layer 3950. Suitable substrate materials include any one or more of: glass; sapphire; magnesium oxide (MgO); mica; polymers (e.g., PET, PEG, polypropylene, polyethylene, etc.); ceramics; fabrics (e.g., cotton, silk, wool); wood; drywall; metal; and combinations thereof.

As previously noted, an electrode (e.g., one of electrodes 3902 and 3912 of FIG. 7) may be either an anode or a cathode. In some embodiments, one electrode may function as a cathode, and the other may function as an anode. Either or both electrodes 3902 and 3912 may be coupled to leads, cables, wires, or other means enabling charge transport to and/or from the device 3900. An electrode may constitute any conductive material, and at least one electrode should be transparent or translucent to EM radiation, and/or be arranged in a manner that allows EM radiation to contact at least a portion of the active layer 3950. Suitable electrode materials may include any one or more of: indium tin oxide or tin-doped indium oxide (ITO); fluorine-doped tin oxide (FTO); cadmium oxide (CdO); zinc indium tin oxide (ZITO); aluminum zinc oxide (AZO); aluminum (Al); gold (Au); calcium (Ca); magnesium (Mg); titanium (Ti); steel; carbon (and allotropes thereof); and combinations thereof.

Mesoporous material (e.g., the material included in mesoporous layer 3904 of FIG. 7) may include any pore-containing material. In some embodiments, the pores may have diameters ranging from about 1 to about 100 nm; in other embodiments, pore diameter may range from about 2 to about 50 nm. Suitable mesoporous material includes any one or more of: any interfacial material and/or mesoporous material discussed elsewhere herein; aluminum (Al); bismuth (Bi); indium (In); molybdenum (Mo); niobium (Nb); nickel (Ni); silicon (Si); titanium (Ti); vanadium (V); zinc (Zn); zirconium (Zr); an oxide of any one or more of the foregoing metals (e.g., alumina, ceria, titania, zinc oxide, zircona, etc.); a sulfide of any one or more of the foregoing metals; a nitride of any one or more of the foregoing metals; and combinations thereof.

Photoactive material (e.g., first or second photoactive material 3906 or 3908 of FIG. 7) may comprise any photoactive compound, such as any one or more of silicon (in some instances, single-crystalline silicon), cadmium telluride, cadmium sulfide, cadmium selenide, copper indium gallium selenide, gallium arsenide, germanium indium phosphide, one or more semiconducting polymers, and combinations thereof. In certain embodiments, photoactive material may instead or in addition comprise a dye (e.g., N719, N3, other ruthenium-based dyes). In some embodiments, a dye (of whatever composition) may be coated onto another layer (e.g., a mesoporous layer and/or an interfacial layer). In some embodiments, photoactive material may include one or more perovskite materials. Perovskite-material-containing photoactive substance may be of a solid form, or in some embodiments it may take the form of a dye that includes a suspension or solution comprising perovskite material. Such a solution or suspension may be coated onto other device components in a manner similar to other dyes. In some embodiments, solid perovskite-containing material may be deposited by any suitable means (e.g., vapor deposition, solution deposition, direct placement of solid material, etc.). Devices according to various embodiments may include one, two, three, or more photoactive compounds (e.g., one, two, three, or more perovskite materials, dyes, or combinations thereof). In certain embodiments including multiple dyes or other photoactive materials, each of the two or more dyes or other photoactive materials may be separated by one or more interfacial layers. In some embodiments, multiple dyes and/or photoactive compounds may be at least in part intermixed.

Charge transport material (e.g., charge transport material of charge transport layer 3910 in FIG. 7) may include solid-state charge transport material (i.e., a colloquially labeled solid-state electrolyte), or it may include a liquid electrolyte and/or ionic liquid. Any of the liquid electrolyte, ionic liquid, and solid-state charge transport material may be referred to as charge transport material. As used herein, "charge transport material" refers to any material, solid, liquid, or otherwise, capable of collecting charge carriers and/or transporting charge carriers. For instance, in PV devices according to some embodiments, a charge transport material may be capable of transporting charge carriers to an electrode. Charge carriers may include holes (the transport of which could make the charge transport material just as properly labeled "hole transport material") and electrons. Holes may be transported toward an anode, and electrons toward a cathode, depending upon placement of the charge transport material in relation to either a cathode or anode in a PV or other device. Suitable examples of charge transport material according to some embodiments may include any one or more of: perovskite material; $I^-/I_3^-$; Co complexes; polythiophenes (e.g., poly(3-hexylthiophene) and derivatives thereof, or P3HT); carbazole-based copolymers such as polyheptadecanylcarbazole dithienylbenzothiadiazole and derivatives thereof (e.g., PCDTBT); other copolymers such as polycyclopentadithiophene—benzothiadiazole and derivatives thereof (e.g., PCPDTBT); poly(triaryl amine) compounds and derivatives thereof (e.g., PTAA); Spiro-OMeTAD; fullerenes and/or fullerene derivatives (e.g., C60, PCBM); and combinations thereof. In certain embodiments, charge transport material may include any material, solid or liquid, capable of collecting charge carriers (electrons or holes), and/or capable of transporting charge carriers. Charge transport material of some embodiments therefore may be n- or p-type active and/or semi-conducting material. Charge transport material may be disposed proximate to one of the electrodes of a device. It may in some embodiments be disposed adjacent to an electrode, although in other embodiments an interfacial layer may be disposed between the charge transport material and an electrode (as shown, e.g., in FIG. 7 with the fifth interfacial layer 3911). In certain embodiments, the type of charge transport material may be selected based upon the electrode to which it is proximate. For example, if the charge transport material collects and/or transports holes, it may be proximate to an anode so as to transport holes to the anode. However, the charge transport material may instead be placed proximate to a cathode, and be selected or constructed so as to transport electrons to the cathode.

As previously noted, devices according to various embodiments may optionally include an interfacial layer between any two other layers and/or materials, although devices according to some embodiments need not contain any interfacial layers. Thus, for example, a perovskite material device may contain zero, one, two, three, four, five, or more interfacial layers (such as the example device of FIG. 7, which contains five interfacial layers 3903, 3905, 3907, 3909, and 3911). An interfacial layer may include a thin-coat interfacial layer in accordance with embodiments previously discussed herein (e.g., comprising alumina and/or other metal-oxide particles, and/or a titania/metal-oxide bilayer, and/or other compounds in accordance with thin-coat interfacial layers as discussed elsewhere herein). An interfacial layer according to some embodiments may include any suitable material for enhancing charge transport and/or collection between two layers or materials; it may also help prevent or reduce the likelihood of charge recombination once a charge has been transported away from one of the materials adjacent to the interfacial layer. Suitable interfacial materials may include any one or more of: any mesoporous material and/or interfacial material discussed elsewhere herein; Al; Bi; In; Mo; Ni; platinum (Pt); Si; Ti; V; Nb; Zn; Zr; oxides of any of the foregoing metals (e.g., alumina, silica, titania); a sulfide of any of the foregoing metals; a nitride of any of the foregoing metals; functionalized or non-functionalized alkyl silyl groups; graphite; graphene; fullerenes; carbon nanotubes; and combinations thereof (including, in some embodiments, bilayers of combined materials). In some embodiments, an interfacial layer may include perovskite material.

A device according to the stylized representation of FIG. 7 may in some embodiments be a PV, such as a DSSC, BHJ, or hybrid solar cell. In some embodiments, devices according to FIG. 7 may constitute parallel or serial multi-cell PVs, batteries, hybrid PV batteries, FETs, LEDS, and/or any other device discussed herein. For example, a BHJ of some embodiments may include two electrodes corresponding to electrodes 3902 and 3912, and an active layer comprising at least two materials in a heterojunction interface (e.g., any two of the materials and/or layers of active layer 3950). In certain embodiments, other devices (such as hybrid PV batteries, parallel or serial multi-cell PVs, etc.) may comprise an active layer including a perovskite material, corresponding to active layer 3950 of FIG. 7. In short, the stylized nature of the depiction of the exemplar device of FIG. 7 should in no way limit the permissible structure or architecture of devices of various embodiments in accordance with FIG. 7.

Additional, more specific, example embodiments of perovskite devices will be discussed in terms of further stylized depictions of example devices. The stylized nature of these depictions, FIGS. 8-9, similarly is not intended to restrict the type of device which may in some embodiments be constructed in accordance with any one or more of FIGS. 8-9. That is, the architectures exhibited in FIGS. 8-9 may be adapted so as to provide the BHJs, batteries, FETs, hybrid PV batteries, serial multi-cell PVs, parallel multi-cell PVs and other similar devices of other embodiments of the present disclosure, in accordance with any suitable means (including both those expressly discussed elsewhere herein, and other suitable means, which will be apparent to those skilled in the art with the benefit of this disclosure).

Figure 8:
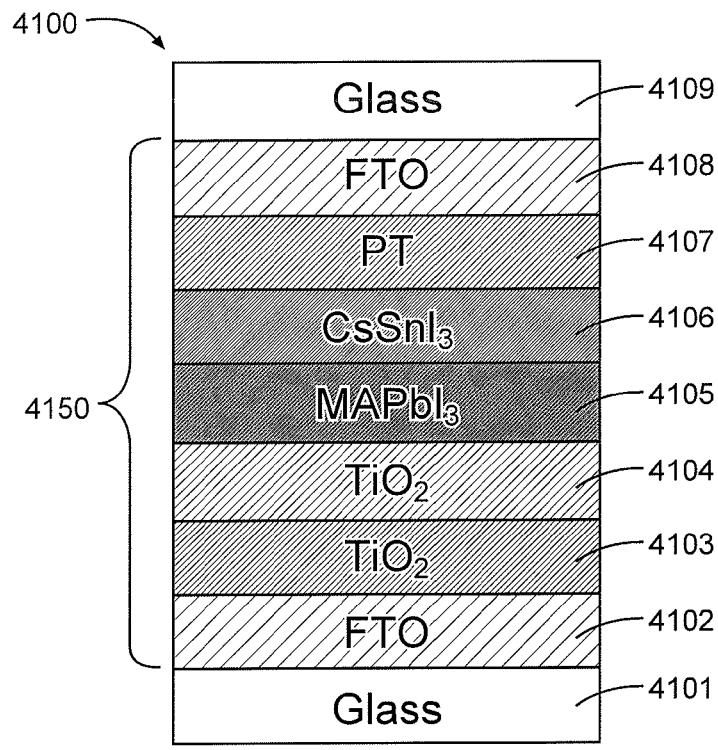
FIG. 8 is a stylized diagram showing components of an exemplar PV device according to some embodiments of the present disclosure.

FIG. 8 depicts an example device 4100 in accordance with various embodiments. The device 4100 illustrates embodiments including first and second glass substrates 4101 and 4109. Each glass substrate has an FTO electrode disposed upon its inner surface (first electrode 4102 and second electrode 4108, respectively), and each electrode has an interfacial layer deposited upon its inner surface: $TiO_2$ first interfacial layer 4103 is deposited upon first electrode 4102, and Pt second interfacial layer 4107 is deposited upon second electrode 4108. Sandwiched between the two interfacial layers are: a mesoporous layer 4104 (comprising $TiO_2$); photoactive material 4105 (comprising the perovskite material $MAPbI_3$); and a charge transport layer 4106 (here comprising $CsSnI_3$).

Figure 9:
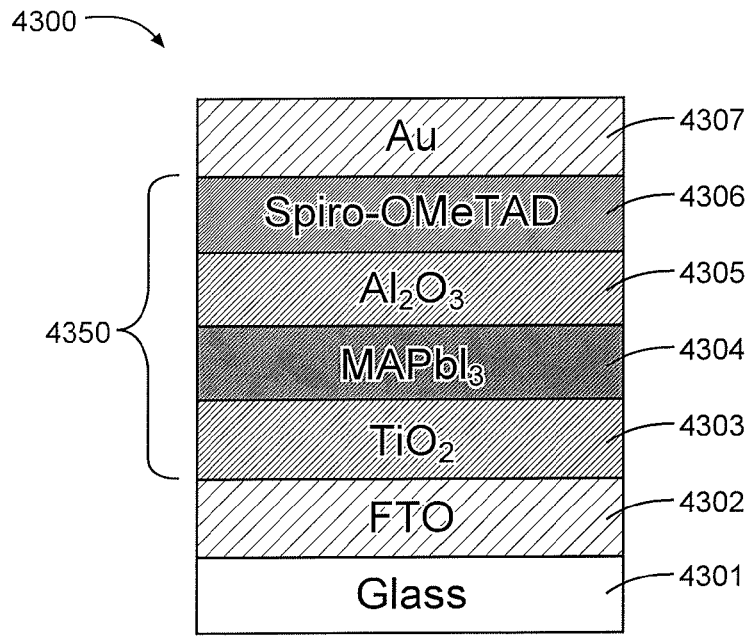
FIG. 9 is a stylized diagram showing components of an exemplar PV device according to some embodiments of the present disclosure.

FIG. 9 depicts an example device 4300 that omits a mesoporous layer. The device 4300 includes a perovskite material photoactive compound 4304 (comprising $MAPbI_3$) sandwiched between first and second interfacial layers 4303 and 4305 (comprising titania and alumina, respectively). The titania interfacial layer 4303 is coated upon an FTO first electrode 4302, which in turn is disposed on an inner surface of a glass substrate 4301. The spiro-OMeTAD charge transport layer 4306 is coated upon an alumina interfacial layer 4305 and disposed on an inner surface of a gold second electrode 4307.

As will be apparent to one of ordinary skill in the art with the benefit of this disclosure, various other embodiments are possible, such as a device with multiple photoactive layers (as exemplified by photoactive layers 3906 and 3908 of the example device of FIG. 7). In some embodiments, as discussed above, each photoactive layer may be separated by an interfacial layer (as shown by third interfacial layer 3907 in FIG. 7). Furthermore, a mesoporous layer may be disposed upon an electrode such as is illustrated in FIG. 7 by mesoporous layer 3904 being disposed upon first electrode 3902. Although FIG. 7 depicts an intervening interfacial layer 3903 disposed between the two, in some embodiments a mesoporous layer may be disposed directly on an electrode.

Additional Perovskite Material Device Examples

Other example perovskite material device architectures will be apparent to those of skill in the art with the benefit of this disclosure. Examples include, but are not limited to, devices containing active layers having any of the following architectures: (1) liquid electrolyte-perovskite material-mesoporous layer; (2) perovskite material-dye-mesoporous layer; (3) first perovskite material-second perovskite material-mesoporous layer; (4) first perovskite material-second perovskite material; (5) first perovskite material-dye-second perovskite material; (6) solid-state charge transport material-perovskite material; (7) solid-state charge transport material-dye-perovskite material-mesoporous layer; (8) solid-state charge transport material-perovskite material-dye-mesoporous layer; (9) solid-state charge transport material-dye-perovskite material-mesoporous layer; and (10) solid-state charge transport material-perovskite material-dye-mesoporous layer. The individual components of each example architecture (e.g., mesoporous layer, charge transport material, etc.) may be in accordance with the discussion above for each component. Furthermore, each example architecture is discussed in more detail below.

As a particular example of some of the aforementioned active layers, in some embodiments, an active layer may include a liquid electrolyte, perovskite material, and a mesoporous layer. The active layer of certain of these embodiments may have substantially the architecture: liquid electrolyte-perovskite material-mesoporous layer. Any liquid electrolyte may be suitable; and any mesoporous layer (e.g., $TiO_2$) may be suitable. In some embodiments, the perovskite material may be deposited upon the mesoporous layer, and thereupon coated with the liquid electrolyte. The perovskite material of some such embodiments may act at least in part as a dye (thus, it may be photoactive).

In other example embodiments, an active layer may include perovskite material, a dye, and a mesoporous layer. The active layer of certain of these embodiments may have substantially the architecture: perovskite material-dye-mesoporous layer. The dye may be coated upon the mesoporous layer and the perovskite material may be disposed upon the dye-coated mesoporous layer. The perovskite material may function as hole-transport material in certain of these embodiments.

In yet other example embodiments, an active layer may include first perovskite material, second perovskite material, and a mesoporous layer. The active layer of certain of these embodiments may have substantially the architecture: first perovskite material-second perovskite material-mesoporous layer. The first and second perovskite material may each comprise the same perovskite material(s) or they may comprise different perovskite materials. Either of the first and second perovskite materials may be photoactive (e.g., a first and/or second perovskite material of such embodiments may function at least in part as a dye).

In certain example embodiments, an active layer may include first perovskite material and second perovskite material. The active layer of certain of these embodiments may have substantially the architecture: first perovskite material-second perovskite material. The first and second perovskite materials may each comprise the same perovskite material (s) or they may comprise different perovskite materials. Either of the first and second perovskite materials may be photoactive (e.g., a first and/or second perovskite material of such embodiments may function at least in part as a dye). In addition, either of the first and second perovskite materials may be capable of functioning as hole-transport material. In some embodiments, one of the first and second perovskite materials functions as an electron-transport material, and the other of the first and second perovskite materials functions as a dye. In some embodiments, the first and second perovskite materials may be disposed within the active layer in a manner that achieves high interfacial area between the first perovskite material and the second perovskite material, such as in the arrangement shown for first and second active material 2810 and 2815, respectively, in FIG. 5 (or as similarly shown by p- and n-type material 2618 and 2620, respectively, in FIG. 4).

In further example embodiments, an active layer may include first perovskite material, a dye, and second perovskite material. The active layer of certain of these embodiments may have substantially the architecture: first perovskite material-dye-second perovskite material. Either of the first and second perovskite materials may function as charge transport material, and the other of the first and second perovskite materials may function as a dye. In some embodiments, both of the first and second perovskite materials may at least in part serve overlapping, similar, and/or identical functions (e.g., both may serve as a dye and/or both may serve as hole-transport material).

In some other example embodiments, an active layer may include a solid-state charge transport material and a perovskite material. The active layer of certain of these embodiments may have substantially the architecture: solid-state charge transport material-perovskite material. For example, the perovskite material and solid-state charge transport material may be disposed within the active layer in a manner that achieves high interfacial area, such as in the arrangement shown for first and second active material 2810 and 2815, respectively, in FIG. 5 (or as similarly shown by p- and n-type material 2618 and 2620, respectively, in FIG. 4).

In other example embodiments, an active layer may include a solid-state charge transport material, a dye, perovskite material, and a mesoporous layer. The active layer of certain of these embodiments may have substantially the architecture: solid-state charge transport material-dye-perovskite material-mesoporous layer. The active layer of certain other of these embodiments may have substantially the architecture: solid-state charge transport material-perovskite material-dye-mesoporous layer. The perovskite material may in some embodiments serve as a second dye. The perovskite material may in such embodiments increase the breadth of the spectrum of visible light absorbed by a PV or other device including an active layer of such embodiments. In certain embodiments, the perovskite material may also or instead serve as an interfacial layer between the dye and mesoporous layer, and/or between the dye and the charge transport material.

In some example embodiments, an active layer may include a liquid electrolyte, a dye, a perovskite material, and a mesoporous layer. The active layer of certain of these embodiments may have substantially the architecture: solid-state charge transport material-dye-perovskite material-mesoporous layer. The active layer of certain other of these embodiments may have substantially the architecture: solid-state charge transport material-perovskite material-dye-mesoporous layer. The perovskite material may serve as photoactive material, an interfacial layer, and/or a combination thereof.

Some embodiments provide BHJ PV devices that include perovskite materials. For example, a BHJ of some embodiments may include a photoactive layer (e.g., photoactive layer 2404 of FIG. 3), which may include one or more perovskite materials. The photoactive layer of such a BHJ may also or instead include any one or more of the above-listed example components discussed above with respect to DSSC active layers. Further, in some embodiments, the BHJ photoactive layer may have an architecture according to any one of the exemplary embodiments of DSSC active layers discussed above.

Figure 6:
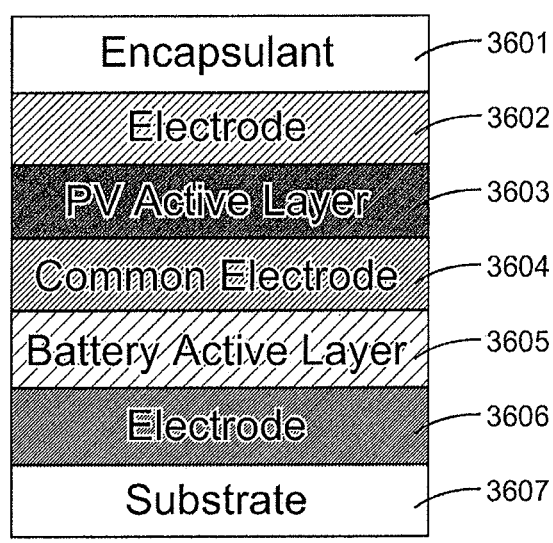
FIG. 6 is a stylized diagram illustrating components of an exemplar PV device according to some embodiments of the present disclosure.

In some embodiments, any PV or other like device may include an active layer according to any one or more of the compositions and/or architectures discussed above. As another example embodiment, an active layer including perovskite material may be included in a multi-photoactive-layer PV cell, such as either or both of the first and second photoactive layers 3701 and 3705 of the exemplary cell shown in the stylized diagram of FIG. 6. Such a multi-photoactive-layer PV cell including an active layer with perovskite material could furthermore be incorporated within a series of electrically coupled multi-photoactive-layer PV cells.

In some embodiments, any of the active layers including perovskite materials incorporated into PVs or other devices as discussed herein may further include any of the various additional materials also discussed herein as suitable for inclusion in an active layer. For example, any active layer including perovskite material may further include an interfacial layer according to various embodiments discussed herein (such as, e.g., a thin-coat interfacial layer). By way of further example, an active layer including perovskite material may further include a light harvesting layer, such as Light Harvesting Layer 1601 as depicted in the exemplary PV represented in FIG. 2.

Formulation of the Perovskite Material Active Layer

As discussed earlier, in some embodiments, a perovskite material may be of the general formula $CwMyXz$, where: C comprises one or more cations (e.g., an amine, ammonium, a Group 1 metal, a Group 2 metal, and/or other cations or cation-like compounds); M comprises one or more metals (examples including Fe, Co, Ni, Cu, Ag, Au, Tl, In, Sb, Sn, Pb, Bi, Ga, Ge, Ti, and Zn); X comprises one or more anions; and w, y, and z represent real numbers between 1 and 20. In some embodiments a pervoskite material in the active layer may have the formulation $CMX_{3-y}X'_{y}$ ($0 \geq y \geq 3$), where: C comprises one or more cations (e.g., an amine, ammonium, a Group 1 metal, a Group 2 metal, and/or other cations or cation-like compounds); M comprises one or more metals (e.g., Fe, Cd, Co, Ni, Cu, Hg, Sn, Pb, Bi, Ge, Ti, Zn, and Zr); and X and X' comprise one or more anions. In one embodiment, the perovskite material may comprise $CPbI_{3-y}Cl_{y}$. In certain embodiments, the perovskite material may be deposited as an active layer in a PV device by, for example, drop casting, spin casting, gravure coating, blade coating, reverse gravure coating, slot-die printing, screen printing, or ink-jet printing onto a substrate layer using the steps described below.

First, a lead halide precursor ink is formed. An amount of lead halide may be massed in a clean, dry vial inside a glove box (i.e., controlled atmosphere box with glove-containing portholes allows for materials manipulation in an air-free environment). Suitable lead halides include, but are not limited to, lead (II) iodide, lead (II) bromide, lead (II) chloride, and lead (II) fluoride. The lead halide may comprise a single species of lead halide or it may comprise a lead halide mixture in a precise ratio. In certain embodiments, the lead halide mixture may comprise any binary, ternary, or quaternary ratio of 0.001-100 mol % of iodide, bromide, chloride, or fluoride. In one embodiment, the lead halide mixture may comprise lead (II) chloride and lead (II) iodide in a ratio of about 10:90 mol:mol. In other embodiments, the lead halide mixture may comprise lead (II) chloride and lead (II) iodide in a ratio of about 5:95, about 7.5:92.5, or about 15:85 mol:mol.

A solvent may then be added to the vial to dissolve the lead solids to form the lead halide precursor ink. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylformamide (DMF). The lead solids may be dissolved at a temperature between about 20° C. to about 150° C. In one embodiment, the lead solids are dissolved at about 85° C. The lead solids may be dissolved for as long as necessary to form a solution, which may take place over a time period up to about 72 hours. The resulting solution forms the base of the lead halide precursor ink. In some embodiments, the lead halide precursor ink may have a lead halide concentration between about 0.001 M and about 10 M. In one embodiment, the lead halide precursor ink has a lead halide concentration of about 1 M. In some embodiments, the lead halide precursor ink may further comprise an amino acid (e.g., 5-aminovaleric acid, histidine, glycine, lycine), an amino acid hydrohalide (e.g., 5-amino valeric acid hydrochloride), an IFL surface-modifying (SAM) agent (such as those discussed earlier in the specification), or a combination thereof.

The lead halide precursor ink may then be deposited on the desired substrate. Suitable substrate layers may include any of the substrate layers identified earlier in this disclosure. As noted above, the lead halide precursor ink may be deposited through a variety of means, including but not limited to, drop casting, spin casting, slot-die printing, screen printing, or ink-jet printing. In certain embodiments, the lead halide precursor ink may be spin-coated onto the substrate at a speed of about 500 rpm to about 10,000 rpm for a time period of about 5 seconds to about 600 seconds. In one embodiment, the lead halide precursor ink may be spin-coated onto the substrate at about 3000 rpm for about 30 seconds. The lead halide precursor ink may be deposited on the substrate at an ambient atmosphere in a humidity range of about 0% relative humidity to about 50% relative humidity. The lead halide precursor ink may then be allowed to dry in a substantially water-free atmosphere, i.e., less than 20% relative humidity, to form a thin film.

The thin film can then be thermally annealed for a time period up to about 24 hours at a temperature of about 20° C. to about 300° C. In one embodiment, the thin film may be thermally annealed for about ten minutes at a temperature of about 50° C. The perovskite material active layer may then be completed by a conversion process in which the precursor film is submerged or rinsed with a solution comprising a solvent or mixture of solvents (e.g., DMF, isopropanol, methanol, ethanol, butanol, chloroform chlorobenzene, dimethylsulfoxide, water) and salt (e.g., methylammonium iodide, formamidinium iodide, guanidinium iodide, 1,2,2-triaminovinylammonium iodide, 5-aminovaleric acid hydroiodide) in a concentration between 0.001M and 10M. In certain embodiments, the thin films can also be thermally post-annealed in the same fashion as in the first line of this paragraph.

In another embodiment, a perovskite material may comprise C'CPbX$_3$, where C' is one or more Group 1 metals (i.e. Li, Na, K, Rb, Cs). In a particular embodiment M' may be cesium (Cs). In another embodiment C' may be rubidium (Rb). In another embodiment C' may be sodium (Na). In another embodiment C' may be potassium (K). In yet other embodiments, a perovskite material may comprise C'$_v$C$_w$Pb$_y$X$_z$, where C' is one or more Group 1 metals and v, w, y, and z represent real numbers between 1 and 20. In certain embodiments, the perovskite material may be deposited as an active layer in a PV device by, for example, drop casting, spin casting, gravure coating, blade coating, reverse gravure coating, slot-die printing, screen printing, or ink-jet printing onto a substrate layer using the steps described below.

First, a lead halide solution is formed. An amount of lead halide may be massed in a clean, dry vessel in a controlled atmosphere environment. Suitable lead halides include, but are not limited to, lead (II) iodide, lead (II) bromide, lead (II) chloride, and lead (II) fluoride. The lead halide may comprise a single species of lead halide or it may comprise a lead halide mixture in a precise ratio. In one embodiment the lead halide may comprise lead (II) iodide. In certain embodiments, the lead halide mixture may comprise any binary, ternary, or quaternary ratio of 0.001-100 mol % of iodide, bromide, chloride, or fluoride. In one embodiment, the lead halide mixture may comprise lead (II) chloride and lead (II) iodide in a ratio of about 10:90 mol:mol. In other embodiments, the lead halide mixture may comprise lead (II) chloride and lead (II) iodide in a ratio of about 5:95, about 7.5:92.5, or about 15:85 mol:mol.

Alternatively, other lead salt precursors may be used in conjunction with or in lieu of lead halide salts to form a lead salt solution. Suitable precursor lead salts may comprise any combination of lead (II) or lead(IV) and the following anions: nitrate, nitrite, carboxylate, acetate, formate, oxylate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

The lead salt solution may further comprise a lead (II) or lead (IV) salt in mole ratios of 0 to 100% to the following metal ions Fe, Cd, Co, Ni, Cu, Hg, Sn, Pb, Bi, Ge, Ti, Zn, and Zr as a salt of the aforementioned anions.

A solvent may then be added to the vessel to dissolve the lead halide solids to form the lead halide solution. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylformamide (DMF). The lead halide solids may be dissolved at a temperature between about 20° C. to about 150° C. In one embodiment, the lead halide solids are dissolved at about 85° C. The lead halide solids may be dissolved for as long as necessary to form a solution, which may take place over a time period up to about 72 hours. The resulting solution forms the base of the lead halide precursor ink. In some embodiments, the lead halide precursor ink may have a lead halide concentration between about 0.001M and about 10M. In one embodiment, the lead halide precursor ink has a lead halide concentration of about 1 M. In some embodiments, the lead halide solution may further comprise an amino acid (e.g., 5-aminovaleric acid, histidine, glycine, lycine), an amino acid hydrohalide (e.g., 5-amino valeric acid hydrochloride), an IFL surface-modifying (SAM) agent (such as those discussed earlier in the specification), or a combination thereof.

Next, a Group 1 metal halide solution is formed. An amount of Group 1 metal halide may be massed in a clean, dry vessel in a controlled atmosphere environment. Suitable Group 1 metal halides include, but are not limited to, cesium iodide, cesium bromide, cesium chloride, cesium fluoride, rubidium iodide, rubidium bromide, rubidium chloride, rubidium fluoride, lithium iodide, lithium bromide, lithium chloride, lithium fluoride, sodium iodide, sodium bromide, sodium chloride, sodium fluoride, potassium iodide, potassium bromide, potassium chloride, potassium fluoride. The Group 1 metal halide may comprise a single species of Group 1 metal halide or it may comprise a Group 1 metal halide mixture in a precise ratio. In one embodiment the Group 1 metal halide may comprise cesium iodide. In another embodiment the Group 1 metal halide may comprise rubidium iodide. In another embodiment the Group 1 metal halide may comprise sodium iodide. In another embodiment the Group 1 metal halide may comprise potassium iodide.

Alternatively, other Group 1 metal salt precursors may be used in conjunction with or in lieu of Group 1 metal halide salts to form a Group 1 metal salt solution. Suitable precursor Group 1 metal salts may comprise any combination of Group 1 metals and the following anions: nitrate, nitrite, carboxylate, acetate, formate, oxylate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

A solvent may then be added to the vessel to dissolve the Group 1 metal halide solids to form the Group 1 metal halide solution. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylsulfoxide (DMSO). The Group 1 metal halide solids may be dissolved at a temperature between about 20° C. to about 150° C. In one embodiment, the Group 1 metal halide solids are dissolved at room temperature (i.e. about 25° C.). The Group 1 metal halide solids may be dissolved for as long as necessary to form a solution, which may take place over a time period up to about 72 hours. The resulting solution forms the Group 1 metal halide solution. In some embodiments, the Group 1 metal halide solution may have a Group 1 metal halide concentration between about 0.001M and about 10M. In one embodiment, the Group 1 metal halide solution has a Group 1 metal halide concentration of about 1 M. In some embodiments, the Group 1 metal halide solution may further comprise an amino acid (e.g., 5-aminovaleric acid, histidine, glycine, lycine), an amino acid hydrohalide (e.g., 5-amino valeric acid hydrochloride), an IFL surface-modifying (SAM) agent (such as those discussed earlier in the specification), or a combination thereof.

Next, the lead halide solution and the Group 1 metal halide solution are mixed to form a thin-film precursor ink. The lead halide solution and Group 1 metal halide solution may be mixed in a ratio such that the resulting thin-film precursor ink has a molar concentration of the Group 1 metal halide that is between 0% and 25% of the molar concentration of the lead halide. In particular embodiments, the thin-film precursor ink may have a molar concentration of the Group 1 metal halide that is 1% of the molar concentration of the lead halide. In particular embodiments, the thin-film precursor ink may have a molar concentration of the Group 1 metal halide that is 5% of the molar concentration of the lead halide. In particular embodiments, the thin-film precursor ink may have a molar concentration of the Group 1 metal halide that is 10% of the molar concentration of the lead halide. In particular embodiments, the thin-film precursor ink may have a molar concentration of the Group 1 metal halide that is 15% of the molar concentration of the lead halide. In particular embodiments, the thin-film precursor ink may have a molar concentration of the Group 1 metal halide that is 20% of the molar concentration of the lead halide. In particular embodiments, the thin-film precursor ink may have a molar concentration of the Group 1 metal halide that is 25% of the molar concentration of the lead halide. In some embodiments the lead halide solution and the Group 1 metal halide solution may be stirred or agitated during or after mixing, The thin-film precursor ink may then be deposited on the desired substrate. Suitable substrate layers may include any of the substrate layers identified earlier in this disclosure. As noted above, the thin-film precursor ink may be deposited through a variety of means, including but not limited to, drop casting, spin casting, gravure coating, blade coating, reverse gravure coating, slot-die printing, screen printing, or ink-jet printing. In certain embodiments, the thin-film precursor ink may be spin-coated onto the substrate at a speed of about 500 rpm to about 10,000 rpm for a time period of about 5 seconds to about 600 seconds. In one embodiment, the thin-film precursor ink may be spin-coated onto the substrate at about 3000 rpm for about 30 seconds. The thin-film precursor ink may be deposited on the substrate at an ambient atmosphere in a humidity range of about 0% relative humidity to about 50% relative humidity. The thin-film precursor ink may then be allowed to dry in a substantially water-free atmosphere, i.e., less than 20% relative humidity, to form a thin film.

The thin film can then be thermally annealed for a time period up to about 24 hours at a temperature of about 20° C. to about 300° C. In one embodiment, the thin film may be thermally annealed for about ten minutes at a temperature of about 50° C. The perovskite material active layer may then be completed by a conversion process in which the precursor film is submerged or rinsed with a salt solution comprising a solvent or mixture of solvents (e.g., DMF, isopropanol, methanol, ethanol, butanol, chloroform chlorobenzene, dimethylsulfoxide, water) and salt (e.g., methylammonium iodide, formamidinium iodide, guanidinium iodide, 1,2,2-triaminovinylammonium iodide, 5-aminovaleric acid hydroiodide) in a concentration between 0.001M and 10M.

In certain embodiments, the perovskite material thin films can also be thermally post-annealed in the same fashion as in the first line of this paragraph.

In some embodiments, the salt solution may be prepared by massing the salt in a clean, dry vessel in a controlled atmosphere environment. Suitable salts include, but are not limited to, methylammonium iodide, formamidinium iodide, guanidinium iodide, imidazolium iodide, ethene tetramine iodide, 1,2,2-triaminovinylammonium iodide, and 5-aminovaleric acid hydroiodide. Other suitable salts may include any organic cation described above in the section entitled "Perovskite Material." The salt may comprise a single species of salt or it may comprise a salt mixture in a precise ratio. In one embodiment the salt may comprise methylammonium iodide. In another embodiment the salt may comprise formamidinium iodide. Next, a solvent may then be added to the vessel to dissolve the salt solids to form the salt solution. Suitable solvents include, but are not limited to, DMF, isopropanol, methanol, ethanol, butanol, chloroform chlorobenzene, dimethylsulfoxide, water, and combinations thereof. In one embodiment, formamidinium iodide salt solids are dissolved in isopropanol. The salt solids may be dissolved at a temperature between about 20° C. to about 150° C. In one embodiment, the salt solids are dissolved at room temperature (i.e. about 25° C.). The salt solids may be dissolved for as long as necessary to form a solution, which may take place over a time period up to about 72 hours. The resulting solution forms the salt solution. In some embodiments, the salt solution may have a salt concentration between about 0.001M and about 10M. In one embodiment, the salt solution has a salt concentration of about 1 M.

For example, using the process described above with a lead (II) iodide solution, a cesium iodide solution, and a methylammonimum (MA) iodide salt solution may result in a perovskite material having the a formula of $Cs_iMAPbI_3$, where i equals a number between 0 and 1. As another example, the using a lead (II) iodide solution, a rubidium iodide solution, and a formamidinium (FA) iodide salt solution may result in a perovskite material having the a formula of $Rb_iFAPbI_3$, where i equals a number between 0 and 1. As another example, the using a lead (II) iodide solution, a cesium iodide solution, and a formamidinium (FA) iodide salt solution may result in a perovskite material having the a formula of $Cs_iFAPbI_3$, where i equals a number between 0 and 1. As another example, the using a lead (II) iodide solution, a potassium iodide solution, and a formamidinium (FA) iodide salt solution may result in a perovskite material having the a formula of $K_iFAPbI_3$, where i equals a number between 0 and 1. As another example, the using a lead (II) iodide solution, a sodium iodide solution, and a formamidinium (FA) iodide salt solution may result in a perovskite material having the a formula of $Na_iFAPbI_3$, where i equals a number between 0 and 1. As another example, the using a lead (II) iodide-lead (II) chloride mixture solution, a cesium iodide solution, and a formamidinium (FA) iodide salt solution may result in a perovskite material having the a formula of $Cs_iFAPbI_{3-y}CL_y$, where i equals a number between 0 and 1 and y represents a number between 0 and 3.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A perovskite material prepared by a process comprising the steps of:
   preparing a thin-film precursor ink, wherein preparing the thin-film precursor ink comprises the steps of:
      introducing a lead halide into a first vessel;
      introducing a first solvent to the first vessel;
      contacting the lead halide with the first solvent to dissolve the lead halide to form a lead halide solution;
      introducing a Group 1 metal halide into a second vessel;
      introducing a second solvent into the second vessel; and
      contacting the Group 1 metal halide with the second solvent to dissolve the Group 1 metal halide to form a Group 1 metal halide solution;
      contacting the lead halide solution with the Group 1 metal halide solution to form the thin-film precursor ink;
   depositing the thin-film precursor ink onto a substrate;
   drying the thin-film precursor ink to form a thin film;
   annealing the thin film; and
   rinsing the thin film with a salt solution comprising a third solvent and a salt selected from the group consisting of methylammonium halide, formamidinium halide, guanidinium halide, ethene tetramine halide, imidazolium halide, 1,2,2-triaminovinyl ammonium halide, and 5-aminovaleric acid hydrohalide.

2. The perovskite material of claim 1, wherein the lead halide comprises lead (II) iodide.

3. The perovskite material of claim 1, wherein the Group 1 metal halide comprises cesium iodide.

4. The perovskite material of claim 1, wherein the Group 1 metal halide comprises rubidium iodide.

5. The perovskite material of claim 1, wherein the Group 1 metal halide comprises sodium iodide.

6. The perovskite material of claim 1, wherein the Group 1 metal halide comprises potassium iodide.

7. The perovskite material of claim 1, wherein the first solvent and the second solvent are selected from the group consisting of dry N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations therof.

8. The perovskite material of claim 1, wherein the first solvent comprises dry dimethylformamide (DMF).

9. The perovskite material of claim 1, wherein the second solvent comprises dimethylsulfoxide (DMSO).

10. The perovskite material of claim 1, wherein the third solvent is selected from the group consisting of dimethylformamide, isopropanol, methanol, ethanol, butanol, chloroform, chlorobenzene, dimethylsulfoxide, water, and combinations thereof.

11. The perovskite material of claim 1, wherein the thin-film precursor ink has a molar concentration of the Group 1 metal halide that is between 1% and 25% of the molar concentration of the lead halide.

12. The perovskite material of claim 1, wherein annealing the thin film occurs for between about 5 to about 30 minutes at a temperature between about 40° C. to about 60° C.

13. The perovskite material of claim 1, wherein the salt comprises formamidinium iodide.

14. The perovskite material of claim 1, wherein the salt comprises methylammonium iodide.

15. The perovskite material of claim 1, wherein rinsing the thin film comprises at least partial submersion in the salt solution.

* * * * *